United States Patent [19]

Wilke et al.

[11] Patent Number: 4,594,447
[45] Date of Patent: Jun. 10, 1986

[54] PROCESS FOR CATALYTIC DIMERIZATION OF ACRYLIC ACID DERIVATIVES

[75] Inventors: Günther Wilke; Karin Sperling; Ludwig Stehling, all of Mulheim am Rhein, Fed. Rep. of Germany

[73] Assignee: Studiengesellschaft Kohle mbH, Mulheim am Rhein, Fed. Rep. of Germany

[21] Appl. No.: 657,292

[22] Filed: Oct. 3, 1984

[30] Foreign Application Priority Data

Oct. 8, 1983 [DE] Fed. Rep. of Germany ....... 3336691

[51] Int. Cl.$^4$ ............................................ C07C 67/343
[52] U.S. Cl. .................... 560/202; 502/155; 502/162; 528/272; 556/7; 556/14; 556/29
[58] Field of Search .................. 560/202; 556/7, 14, 556/29; 502/162, 155; 562/592

[56] References Cited

U.S. PATENT DOCUMENTS

| | | | |
|---|---|---|---|
| 2,232,785 | 2/1941 | Howk | 560/202 X |
| 3,013,066 | 12/1961 | Alderson | 560/202 |
| 3,074,999 | 1/1963 | Rauhut et al. | 560/202 |
| 3,417,130 | 12/1968 | Pruett et al. | 560/202 |
| 4,451,665 | 5/1984 | Nugent | 560/202 |

*Primary Examiner*—Natalie Trousof
*Assistant Examiner*—Vera C. Clarke
*Attorney, Agent, or Firm*—Sprung Horn Kramer & Woods

[57] ABSTRACT

The invention relates to a process for the dimerization of derivatives of acrylic acid in the homogeneous phase which process is characterized in that a compound having the general formula $H_2C=CR^1\text{-}COOR^2$, wherein $R^1$ represents H or a linear alkyl group having from 1 to 3 carbon atoms and $R^2$ represents a linear alkyl group having from 1 to 3 carbon atoms, is reacted in a solvent at a temperature of from $-50°$ C. to $+50°$ C. in the presence of nickel compounds as catalysts which contain complex anions X in a molar ratio Ni:X=1:1 and organic or hydride ligands and are modifed with phosphanes having the general formula $PR_2R'$, wherein R and R' may be same or different and represent alkyl residues having from 1 to 8 carbon atoms or phenyl residues, as well as the use of the dimers formed in the dimerization.

7 Claims, No Drawings

PROCESS FOR CATALYTIC DIMERIZATION OF ACRYLIC ACID DERIVATIVES

The present invention relates to a process for the catalytic dimerization of derivatives of acrylic acid, i.e. to the preparation of dicarbonic acid derivatives which still contain one double bond. The products obtainable according to the invention are valuable monomers useful for the preparation of polymers. According to the claimed process, more specifically, linear dimers can be prepared with high selectivity.

It has been known that tertiary phosphanes, phosphites and certain tertiary amines are capable of dimerizing acrylic acid derivatives, in which process, however, branched dimers are preferably formed, such as, e.g., α-methylene glutaric acid methyl ester from acrylic acid methyl ester.

It has further been known that palladium(II) or rhodium(III) compounds dimerize acrylic acid methyl ester in the heat and under pressure, while the yield, however, is less than 70% and the selectivity for obtaining linear dimers is very small.

It has also been known that rhodium(III) compounds dimerize acrylic amide in boiling ethanol very slowly and with bad yield.

Moreover, it has been known that acrylonitrile and acrylic acid esters are converted into dihydro dimers and numerous by-products under $H_2$ pressure in the heat under the influence of ruthenium compounds.

Eventually, it has been known that soluble palladium(II) complexes in combination with quinones dimerize unsaturated carboxylic acid derivatives having the general formula $CH_2=CH-COOR-$ at a temperature from 0° C. to the boiling point of the substrates.

All of the known processes are only restrictedly feasible under technical aspects, as either only branched products are formed (phosphanes etc.), or catalysts based on extremely expensive metals (Pd, Rh, Ru) must be employed which—what is particularly disadvantageous—do only yield small numbers of cycles (a maximum of about 45 dimerization steps per molecule of catalyst or per metal atom, respectively).

Said drawbacks inherent to the known processes are overcome by the process according to the present invention by using catalysts based on an inexpensive transition metal (Ni) under mild conditions which enable a high selectivity with respect to the linear dimers and, at the same time, high numbers of cycles (in excess of 300 moles of dimer per mole of catalyst) to be obtained.

Accordingly, it is the object of the invention to provide a process for the dimerization of derivatives of acrylic acid in the homogeneous phase which process is characterized in that a compound having the general formula $H_2C=CR^1-COOR^2$, wherein $R^1$ represents H or a linear alkyl group having from 1 to 3 carbon atoms and $R^2$ represents a linear alkyl group having from 1 to 3 carbon atoms, is reacted in a solvent at a temperature of from $-50°$ C. to $+50°$ C. in the presence of nickel compounds as catalysts which contain complex anions X in a molar ratio Ni:X=1:1 and organic or hydride ligands and are modified with phosphanes having the general formula $PR_2R'$, wherein R and R' may be same or different and represent alkyl residues having from 1 to 8 carbon atoms or phenyl residues, as well as the use of the dimers formed in the dimerization.

The catalysts used in the process according to the invention are soluble nickel compounds containing complex anions X. The complex anions, more specifically, may be, fluorine-containing anions such as, e.g., $BF_4^-$, $PF_6^-$ or $SbF_6^-$. In the nickel compounds employed as the catalysts said fluoro complexes are present in a molar ratio of nickel to the complex anion X of 1:1.

The soluble nickel compounds in addition contain alkyl, cycloalkyl, aralkyl, allyl, cycloalkenyl, or aryl groups or a hydride ion as ligands. Among these, preferred ligands are the $\eta^3$-allyl group, the $\eta^3$-cyclooctenyl group or optionally alkyl-substituted phenyl groups such as the mesityl residue.

The soluble catalyst systems further contain phosphanes having the general formula $PR_2R'$, wherein R and R' may be same or different and represent linear alkyl residues having from 1 to 8 carbon atoms or phenyl residues, as modifying ligands. Tri-n-alkyl phosphanes, in particular trimethyl phosphane, are preferably used. The molar ratio of Ni:phosphane is 1:0.5 to 1.5, and preferably 1:1.

The catalysts of the process according to the invention are accessible by several routes. Thus, for example, catalysts may be prepared from $\eta^3$-allyl nickel halides or the 1:1 phosphane adducts thereof, respectively, and the silver salts of said complex anions:

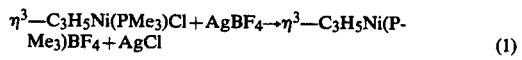

$$\eta^3\text{—}C_3H_5Ni(PMe_3)Cl + AgBF_4 \rightarrow \eta^3\text{—}C_3H_5Ni(PMe_3)BF_4 + AgCl \qquad (1)$$

Another possibility of preparing the catalyst is the reaction of bis($\eta^3$-allyl)nickel compounds with the acids of said complex anions X, e.g.

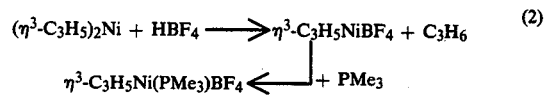

Active catalysts are also obtained by a reaction of complex anions in the way of an oxidative addition, e.g. of bis(cyclooctadiene)nickel(O)($COD_2Ni$) and HX.

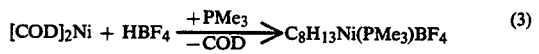

The complex compound formed by this route contains a $C_8H_{13}$ group besides the complex anion.

The complexes analogously containing aryl groups are obtained by reaction of the corresponding nickel diaryls with HX, e.g.

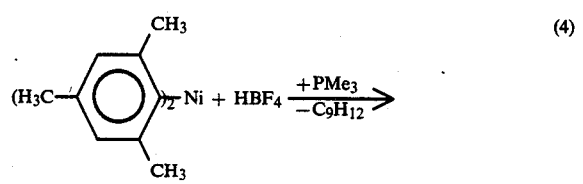

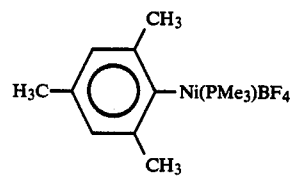

It is assumed that in the course of the catalytic dimerization the organic residues contained in the initial complexes are detached, so that a $HNi(PMe_3)BF_4$ is formed as the actually active catalyst species which during the catalysis cycle is converted by addition of the HNi group to an unsaturated monomer into a R—Ni group, e.g. a MeOCOCH$_2$—CH$_2$—Ni group, which by addition of the Ni—C bond to a further monomer and $\beta$—H elimination and removal of dimer again regenerates the hydride HNi(PMe$_3$)BF$_4$ which in turn directly enters the next cycle.

By means of the catalysts as exemplified, for example, acrylic acid esters having the general formula CH$_2$=CH—CO$_2$R$^2$, wherein R$^2$ represents alkyl residues having 1 to 3 carbon atoms, and preferably alkyl residues having 1 or 2 carbon atoms, respectively, can be converted into linear dimers having one double bond in the 2- or 3-positions, respectively, with a high selectivity (>90%). Small amounts of branched mono-unsaturated dicarboxylic acid esters are obtained as by-products. Higher oligomers and/or polymers, respectively, are virtually not formed. Analogously, the dimerization of the esters of methacrylic acid (R$^1$=CH$_3$, R$^2$=CH$_3$, C$_2$H$_5$) can successfully be carried out with high specifity according to the present invention.

The dimerization is preferably carried out in polar solvents such as, e.g. methylene chloride or chlorobenzene, while the attainable number of cycles increases with an increasing dilution of the catalyst.

The dimerization may be carried out in temperature range of from $-50°$ C. to $+50°$ C., and preferably at a temperature of from $-20°$ C. to $+20°$ C.

The predominantly linear dicarboxylic acid esters having one double bond in the 2- or 3-positions, respectively, preparable according to the invention with a high selectivity may be used as valuable monomers for the preparation of polyamides and/or polyesters, respectively. The polymers formed in the course of the polycondensation reactions are capable of being cross-linked due to the presence of the double bonds therein and thereby enable the production of polymers for use in many fields of application. On the other hand, the process according to the invention opens a novel, economically interesting access to adipic acid and the esters thereof, as the linear dimers of the acrylic acid can smoothly be hydrogenated.

The present invention is further illustrated by, but not limited to, the following examples. All of the experiments described in the examples were carried out under argon as protective gas.

EXAMPLE 1

0.29 g (2,06 mmol) of ($\eta^3$—C$_3$H$_5$)$_2$Ni in 50 ml of CH$_2$Cl$_2$ together with 0.19 ml=0.14 g (1.85 mmol) of trimethyl phosphane (PMe$_3$) at $-78°$ C. were reacted 0.181 g (2.059 mmol) HBF$_4$, i.e. 0.28 ml of a 54% ethereal solution thereof. After 30 minutes at $-78°$ C. said catalyst solution was allowed to flow into a solution cooled to 0° C. of 192 g (2.4 mol) of acrylic acid methyl ester (AME) in 400 ml CH$_2$Cl$_2$ (Ni:AME=1:1082). After 46 hours all volatile products were evaporated in vacuo. Substantially only the employed amount of catalyst besides traces of non-volatile compounds were left as residue. The conversion as indicated by gas chromatography (GC) was 71%, i.e. 136 g of AME were dimerized. The distillate contained 122 g of linear and 14 g of branched mono-unsaturated di-esters besides 56 g of AME. Thus, the selectivity, based on linear diesters, was 90%. Hence, 692 moles of AME were dimerized per mole of nickel atoms, or 346 cycles were passed.

EXAMPLE 2

The experiment was carried out in the same manner as Example 1, however samples were taken at intervals in order to determine the respective degree of conversion:

| Sampling after hrs. | Conversion % | % Selectivity, based on linear esters |
|---|---|---|
| 2 | 26 | 91 |
| 4 | 35 | 92 |
| 8 | 50 | 92.5 |
| 22 | 61 | 92 |
| 46 | 65 | 92 |
| 70 | 69 | 92 |

622 moles of AME per mole of nickel were converted, i.e. 311 cycles were passed.

EXAMPLE 3

0.530 g (2.39 mmol) of C$_{12}$H$_{18}$Ni prepared according to the reaction equation

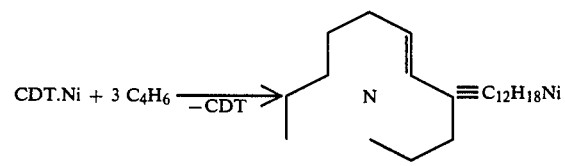

in 50 ml of CH$_2$Cl$_2$ together with 0.22 ml=0.164 g (2.15 mmol) of PMe$_3$ were reacted at $-78°$ C. with 0.21 g (2.39 mmol) of HBF$_4$, i.e. 0.33 ml of a 54% ethereal solution, and after 30 minutes charged into a solution cooled to 0° C. of 192 g (2.30 mol) of AME in 450 ml of CH$_2$Cl$_2$ (Ni:AME=1:962). In the same manner as in Example 2 samples were analyzed by gas chromatography:

| Sampling after hrs. | Conversion % | % Selectivity, based on linear esters |
|---|---|---|
| 2 | 7.8 | 92 |
| 4 | 15 | 92 |
| 8 | 30.5 | 92 |
| 20 | 50.5 | 92 |
| 46 | 64 | 92 |
| 70 | 69 | 91 |
| 94 | 71 | 91 |
| 118 | 78 | 91 |

In total, 672 moles of AME per mole of nickel were converted, i.e. 336 cycles were passed.

EXAMPLE 4

The experiment was carried out as in Example 1, however using 0.6 g (2.2 mmol) of bis(cyclooctadiene)-nickel(O)(COD$_2$Ni) and equivalent amounts of HBF$_4$ and PMe$_3$, Ni:AME=1:1000. After 8 hours the conversion was 11%, and the selectivity, based on linear diester, was 90%.

EXAMPLE 5

0.39 g (2 mmol) of AgBF$_4$ were suspended in 10 ml of CH$_2$Cl$_2$, and at $-30°$ C. a solution of 0.42 g (2 mmol) of $\eta^3$—C$_3$H$_5$NiCl(PMe$_3$) in 30 ml of CH$_2$Cl$_2$ were added thereto. After 90 minutes, 17 g (0.2 mol) of AME (pre-cooled to 0° C.) were added at 0° C. (Ni:AME=1:100).

After 10 hours, there was worked up and analyzed as indicated in Example 1. A conversion of 83.5% and a selectivity of 90%, based on linear dimers, were found. The linear dimers were composed of 93.8% of trans-hexene-2-diacid dimethylester, 5.4% of cis-hexene-2-diacid dimethylester, 1.3% of trans-hexene-3-diacid dimethylester. In total, 42 cycles per nickel atom were passed.

EXAMPLES 6-8

Procedure as in Example 5, however with use of equivalent amounts of the following phosphanes in the place of $PMe_3$: $P(n-C_4H_9)_3$ (Example 6), $P(n-C_8H_{17})_3$ (Example 7), $C_6H_5P(CH_3)_2$ (Example 8).

| Example | Phosphane | % Conversion after 10 hrs. | Number of cycles | % Selectivity based on linear dimers |
|---|---|---|---|---|
| 5 | $P(CH_3)_3$ | 83.5 | 42 | 90 |
| 6 | $P(n-C_4H_9)_3$ | 70.5 | 35 | 87 |
| 7 | $P(n-C_8H_{17})_3$ | 49.5 | 25 | 86 |
| 8 | $C_6H_5P(CH_3)_2$ | 48.1 | 25 | 85 |

EXAMPLES 9-10

Procedure as in Example 5, however with use of equivalent amounts of $AgPF_6$ (Example 9) and $AgSbF_6$ (Example 10).

| Example | Anion | % Conversion after 10 hrs. | Number of cycles | % Selectivity based on linear dimers |
|---|---|---|---|---|
| 5 | $BF_4$ | 83.5 | 42 | 90 |
| 9 | $PF_6$ | 46.3 | 23 | 91 |
| 10 | $SbF_6$ | 46.2 | 23 | 87 |

EXAMPLES 11-13

Procedure as in Example 5, however with use of various solvents:

| Example | Solvent | % Conversion after 10 hrs. | Number of cycles | % Selectivity based on linear dimers |
|---|---|---|---|---|
| 5 | $CH_2Cl_2$ | 83.5 | 42 | 90 |
| 11 | Chlorobenzene | 30.1 | 15 | 89 |
| 12 | Nitrobenzene | 50.8 | 25 | 88 |
| 13 | Toluene | 27 | 13 | 91 |

EXAMPLES 14-17

Procedure as in Example 5, however operation at various temperatures:

| Example | Temperature, °C. | % Conversion after 10 hrs. | Number of cycles | % Selectivity based on linear dimers |
|---|---|---|---|---|
| 14 | −20 | 8 | 15 | 87 |
| 15 | 0 | 8 | 41 | 90 |
| 16 | +20 | 2 | 29 | 87 |
| 17 | +20 | 6 | 33 | 89 |

EXAMPLES 18-20

The preparation of the catalyst was done as in Example 1, whereas the catalysis reactions were carried out at different temperatures and concentrations (RT=Reaction Time):

| Ex. | Temp. °C. | RT h | Ni:$CH_2Cl_2$ mmol/ml | Ni:AME mmol/mmol | Cycle number | % Selectivity |
|---|---|---|---|---|---|---|
| 18 | −10 | 312 | 1/176 | 1:1792 | 165 | 91 |
| 19 | 0 | 73 | 1/202 | 1:1082 | 383 | 90 |
| 20 | +10 | 120 | 1/430 | 1:2269 | 219 | 90 |

EXAMPLES 21-25

The procedure was the same as in Example 5, however operation at different concentrations of $CH_2Cl_2$ and AME; reaction conditions: 8 h, room temperature.

| Example | Ni:$CH_2Cl_2$ mmol/ml | Ni:AME mmol/mmol | Number of cycles | % Selectivity based on linear dimers |
|---|---|---|---|---|
| 21 | 1/7.1 | 1:507 | 17 | 85 |
| 22 | 1/75 | 1:314 | 100 | 85 |
| 23 | 1/104 | 1:404 | 111 | 91 |
| 24 | 1/219 | 1:371 | 126 | 88 |
| 25 | 1/440 | 1:590 | 144 | 96 |

EXAMPLES 26-28

Procedure as in Example 5, however with use of methacrylic acid methylester (MAME) in the place of AME. As indicated by GC, the distillate contained 2,5-dimethylhexene(2)-diacid dimethylester (2,5-Dime-2-HDM) as the main product (of linear and branched dimers) in addition to unreacted MAME.

| Example | Temp. | RT h | Number of cycles | % 2,5-Dime-2-HDM based on reacted MAME) |
|---|---|---|---|---|
| 26 | 0° C. | 10 | 4 | 87 |
| 27 | Room Temp. | 10 | 9 | 79 |
| 28 | Room Temp. | 20 | 13 | 83 |

EXAMPLE 29

0.44 g (2.07 mmol) of $(\eta^3C_3H_5)NiCl(PMe_3)$ were stirred in 50 ml of chlorobenzene with 0.40 g (2.07 mmol) $AgBF_4$ at −30° C. for 1.5 hours. 68.4 g (0.79 mol) of acrylic acid methyl ester (AME) were allowed to flow into the catalyst solution. (Ni:AME=1:385), and the mixture was heated to 50° C. After 6 hours all volatile products were withdrawn in vacuo. As indicated by gas chromatography, the conversion amounted to 17.03%, i.e. 11,6 g of AME were dimerized. The distillate contained 10.2 g of linear and 1.4 g of branched monomeric di-esters in addition to 56.7 g AME. The selectivity, based on linear di-esters was 87.8%. Accordingly, 58 moles of AME were dimerized per mole of nickel, or 29 cycles were passed, respectively.

What is claimed is:

1. A process for the catalytic dimerization of derivatives of acrylic acid in the homogeneous phase, characterized in that a compound having the formula $H_2C=CR^1-COOR^2$, wherein $R^1$ represents H or a linear alkyl group having from 1 to 3 carbon atoms and $R^2$ represents a linear alkyl group having from 1 to 3 carbon atoms, is reacted in a solvent at a temperature of from $-50°$ C. to $+50°$ C. in the presence of nickel compounds as catalysts which contain complex anions X in a molar ratio Ni:X=1:1 and organic or hydride ligands and are modified with phosphanes having the formula $PR_2R'$, wherein R and R' may be same or different and represent alkyl residues having from 1 to 8 carbon atoms or phenyl residues.

2. The process according to claim 1, characterized in that acrylic acid methyl ester or methacrylic acid methyl ester are used as monomers.

3. The process according to claim 1, characterized in that the soluble nickel compounds contain alkyl, cycloalkyl, aralkyl, allyl, cycloalkenyl, or aryl groups or hydride ions as further anions.

4. The process according to claim 1, characterized in that soluble nickel compounds containing $BF_4$-, $PF_6$- or $SbF_6$-anions as complex anions X are used as the catalysts.

5. The process according to claim 1, characterized in that tri-n-alkyl phosphanes $PR_2R'$, wherein R and R' are the same and represent linear alkyl residues having from 1 to 8 carbon atoms, and preferably trimethyl phosphane, in a molar ratio of Ni:$PR_2R'$ of from 1:0.5 to 1.5 are used for modifying the soluble nickel compounds.

6. The process according to claim 1, characterized in that the dimerization is carried out in methylene chloride.

7. The process according to claim 1, characterized in that temperatures of from $-20°$ C. to $+20°$ C. are employed.

* * * * *

UNITED STATES PATENT AND TRADEMARK OFFICE
CERTIFICATE OF CORRECTION

PATENT NO. : 4,594,447
DATED : June 10, 1986
INVENTOR(S) : Günther Wilke, et al.

It is certified that error appears in the above-identified patent and that said Letters Patent is hereby corrected as shown below:

Col. 4, line 27　　　　　Delete structure in middle of formula and substitute:

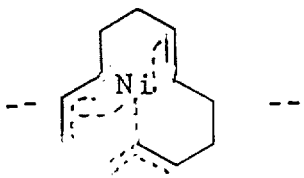

Col. 6, line 50　　　　　Delete " = " and substitute -- $\hat{=}$ --
Title Page, No. 75　　　Delete "Rhein" and substitute
"Inventors", line 3, &　　--Ruhr--
No. 73 "Assignee,
line 2

Signed and Sealed this

Tenth Day of February, 1987

Attest:

DONALD J. QUIGG

Attesting Officer　　　　Commissioner of Patents and Trademarks